| United States Patent [19] | [11] | 4,423,268 |
|---|---|---|
| Miller | [45] | Dec. 27, 1983 |

[54] LOW PRESSURE OLIGOMERIZATION OF GASEOUS OLEFINS

[75] Inventor: Stephen J. Miller, San Francisco, Calif.

[73] Assignee: Chevron Research Company, San Francisco, Calif.

[21] Appl. No.: 338,178

[22] Filed: Jan. 8, 1982

[51] Int. Cl.$^3$ .............................................. C07C 2/02
[52] U.S. Cl. .................................... 585/533; 585/530
[58] Field of Search ................ 585/517, 530, 533, 510

[56] References Cited

U.S. PATENT DOCUMENTS

| 4,238,318 | 12/1980 | Kouwenhoven et al. | 208/137 |
| 4,289,607 | 9/1981 | Kokotailo | 585/533 |
| 4,324,940 | 4/1982 | Dessau | 585/333 |

*Primary Examiner*—Curtis R. Davis
*Attorney, Agent, or Firm*—D. A. Newell; S. R. La Paglia; W. L. Stumpf

[57] ABSTRACT

A process for oligomerizing normally gaseous olefins over essentially alumina free molecular sieves at low pressures is disclosed.

10 Claims, 1 Drawing Figure

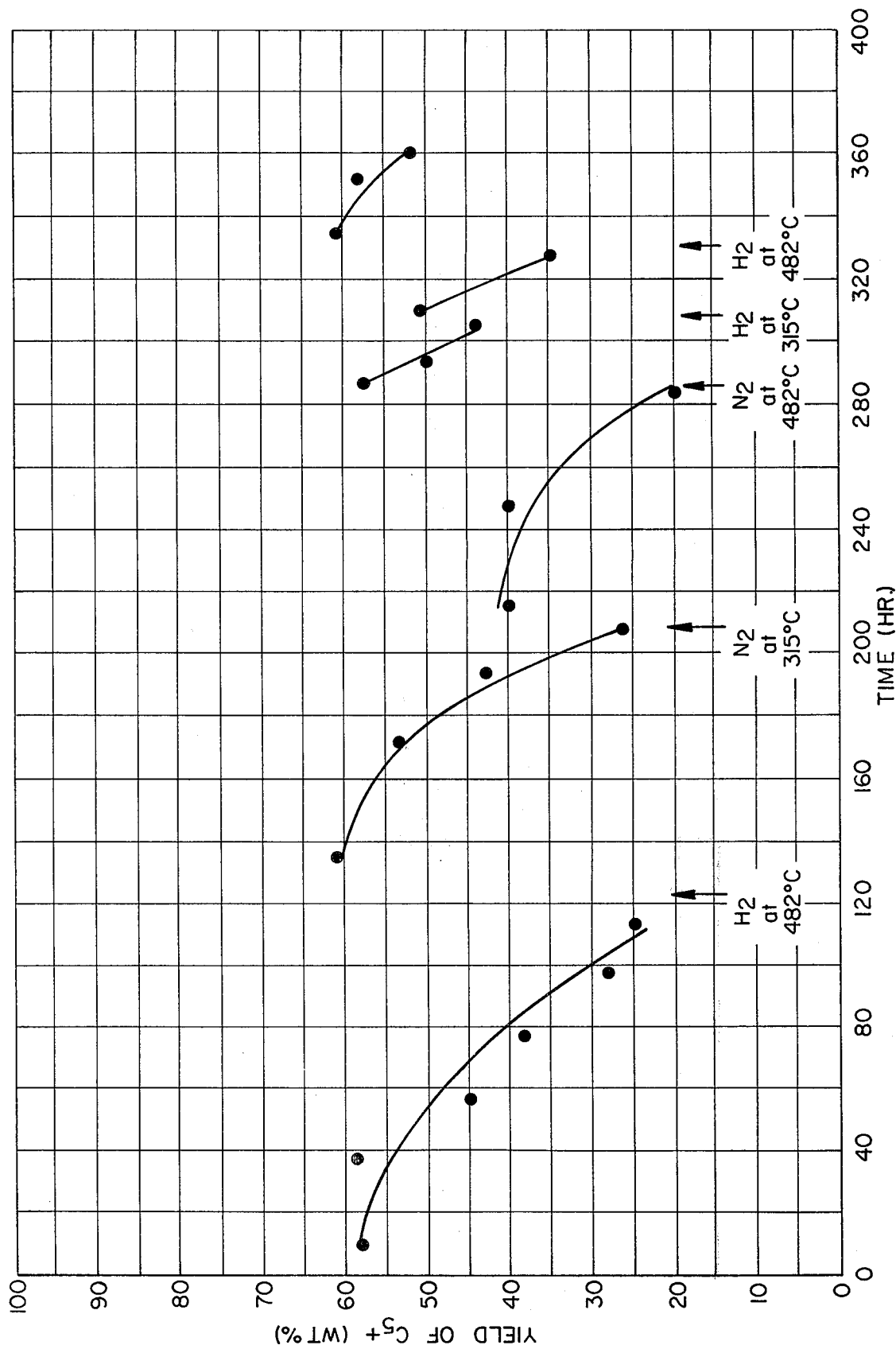

LOW PRESSURE OLIGOMERIZATION OF GASEOUS OLEFINS

TECHNICAL FIELD

Light alkenes, especially propene and butenes, are light gas products from a large number of synthetic processes performed in the petroleum refinery. They are produced as offgases in catalytic cracking and as products of synthetic fuel preparation techniques.

It can be appreciated that there is a continuing search for more efficient methods for using light olefins and for converting them to heavier, more valuable liquid olefins.

A number of patents relating to preparing gasoline range olefin oligomers using highly active zeolites such as ZSM-5 have issued (e.g., U.S. Pat. No. 3,827,968, Givens et al., Aug. 6, 1974; U.S. Pat. No. 3,960,978, Givens et al., June 1, 1976 U.S. Pat. No. 4,227,992, Garwood et al., Oct. 14, 1980; U.S. Pat. No. 4,211,640, Garwood et al., July 8, 1980). Low aluminum content metal organosilicates are disclosed for use in other hydrocarbon conversion processes, U.S. Pat. No. 3,941,871, Dwyer et al., Mar. 2, 1976, and as adsorbents U.S. Pat. No. 4,061,724, Grose et al., Dec. 6, 1977.

Even with the existence of these zeolitic oligomerization processes, it can be appreciated that there is a continuing search for efficient methods of liquid olefin preparation which use available materials, do not require solvent recovery steps or use of liquid solutions, and yet which are efficient.

I have discovered that the short chain alkenes can be polymerized over essentially alumina free intermediate pore size crystalline molecular sieves to highly desirable, normally liquid, longer chain alkenes at low pressures. Surprisingly, these essentially alumina free materials can catalyze these reactions to a high degree even though they have extremely low aluminum contents.

TECHNICAL DISCLOSURE

My discovery is embodied in a process for oligomerizing normally gaseous alkenes, comprising:

(a) contacting under low pressure oligomerization conditions a feed comprising normally gaseous alkenes with a catalyst comprising an essentially alumina free intermediate pore size silicaceous crystalline molecular sieve; and (b) recovering an effluent comprising oligomers of said alkenes.

The feeds used in the present process contain normally gaseous alkenes with 2 to 6 carbon atoms. The alkene chains can be branched. And, even though intermediate pore size molecular sieves are used as catalysts, alkenes, such as 3,3-dimethyl-1-butene, which have quaternary carbons (two branches on the same carbon atom) can be used. The preferred alkenes are straight chain, or n-alkenes, and the preferred n-alkenes are 1-alkenes. The most preferred alkenes are the compounds propene, 1-butene, 2-butene and 2-methylpropene as well as mixtures of them.

The feed alkenes can be prepared from any source by standard methods. Sources of feed alkenes can include FCC offgas, coker offgas, thermal cracking offgas, syngas (by use of CO reduction catalysts), low pressure, nonhydrogenative zeolitic dewaxing, alkanols (using high silica zeolites), and dewaxing with crystalline silica polymorphs. The alkenes can be in hydrocarbon streams with other hydrocarbonaceous compounds, but preferably, the feed is primarily alkenes.

By "essentially alumina free intermediate pore size silicaceous crystalline molecular sieve," as used herein, is meant silica containing materials which contain relatively insignificant amounts of alumina. These crystalline materials can include crystalline silica polymorphs, e.g. silicalite, chromia silicates, e.g. CZM, and ferrosilicates, e.g. U.S. Pat. No. 4,238,318.

All of these materials have the ability of sorting molecules based on the size or the shape, or both, of the molecules. The larger pore size materials will admit larger molecules than the smaller pore size materials. Intermediate pore size silicaceous crystalline molecular sieves have the unique characteristics of being able to differentiate between large molecules and molecules containing quaternary carbon atoms on the one hand, and smaller molecules on the other. Thus, the intermediate pore size materials have surprising molecule sieving characteristics by reason of their effective pore apertures, when compared to larger pore size crystalline molecule sieves.

By "intermediate pore size," as used herein, is meant as effective pore aperture in the range of about 5 to 6.5 Angstroms when the molecular sieve is in the H-form. Molecular sieves having pore apertures in this range tend to have unique molecular sieving characteristics. Unlike small pore zeolites such as erionite and chabazite, they will allow hydrocarbons having some branching into the molecular sieve void spaces. Unlike larger pore zeolites such as the faujasites, they can differentiate between n-alkenes and slightly branched alkanes on the one hand and larger branched alkanes having, for example, quaternary carbon atoms.

The effective pore size of the molecular sieves can be measured using standard adsorption techniques and hydrocarbonaceous compounds of known minimum kinetic diameters. See Breck, *Zeolite Molecular Sieves,* 1974 (especially Chapter 8) and Anderson et al, J. Catalysis 58, 114 (1979), both of which are incorporated by reference.

Intermediate pore size molecular sieves in the H-form will typically admit molecules having kinetic diameters of 5.0 to 6.5 Angstroms with little hindrance. Examples of such compounds (and their kinetic diameters in Angstroms) are: n-hexane (4.3), 3-methylpentane (5.5), benzene (5.85), and toluene (5.8). Compounds having kinetic diameters of about 6 to 6.5 Angstroms can be admitted into the pores, depending on the particular sieve, but do not penetrate as quickly and in some cases are effectively excluded. Compounds having kinetic diameters in the range of 6 to 6.5 Angstroms include: cyclohexane (6.0), 2,3-dimethylbutane (6.1), m-xylene (6.1), and 1,2,3,4-tetramethylbenzene (6.4). Generally, compounds having kinetic diameters of greater than about 6.5 Angstroms do not penetrate the pore apertures and thus are not absorbed into the interior of the moleculer sieve lattice. Examples of such larger compounds include: o-xylene (6.8), hexamethylbenzene (7.1), 1,3,5-trimethylbenzene (7.5), and tributylamine (8.1).

The preferred effective pore size range is from about 5.3 to about 6.2 Angstroms. Among the materials falling within this range are silicalite, the RE 29,948 organosilicates, and the chromia silicate CZM.

In performing adsorption measurements to determine pore size, standard techniques are used. It is convenient to consider a particular molecule as excluded if it does not reach at least 95% of its equilibrium adsorption value on the zeolite in less than about 10 minutes (p/po=0.5; 25° C.).

"Essentially alumina free," as used herein, is meant the product silica polymorph (or essentially alumina-free silicaceous crystalline molecular sieve) has a silica:alumina mole ratio of greater than about 200:1, preferably greater than 500:1, and more preferably greater than 1000:1. The phrase "essentially alumina free" is used because it is difficult to prepare completely aluminum free reaction mixtures for synthesizing these materials. Especially when commercial silica sources are used, aluminum is almost always present to a greater or lesser degree. The hydrothermal reaction mixtures from which the essentially alumina free crystalline silicaceous molecular sieves are prepared can also be referred to as being substantially aluminum free. By this usage is meant that no aluminum is intentionally added to the reaction mixture, e.g., as an alumina or aluminate reagent, and that to the extent aluminum is present, it occurs only as a contaminate in the reagents.

Intermediate pore size crystalline silicas include silicalite, as disclosed in U.S. Pat. No. 4,061,724; "RE 29,948 organosilicates" as disclosed in RE 29,948; and CZH-9, Ser. No. 264,767, Hickson, filed May 18, 1981. Intermediate pore size silicas, ferrosilicates and gallio-silicates are disclosed in U.S. Pat. No. 4,238,318, Kouwenhoven et al, Dec. 9, 1980. Intermediate pore size chromia silicates, CZM, are disclosed in Ser. No. 160,618, Miller, filed June 28, 1980. All of these disclosures are incorporated by reference.

The most preferred molecular sieves are silicalite, the RE 29,948 organosilicates, and CZM. Of course, these and other molecular sieves can be used in physical admixtures.

Surprisingly, the silicaceous crystalline molecular sieve catalysts can be made substantially more active and stable for oligomerization by including the Group IIB metals, zinc or cadmium. A primary characteristic of these substituents is that they are weak bases, and are not easily reduced. These metals can be incorporated into the catalysts using standard impregnation, ion exchange, etc., techniques. Other metals such as calcium and the rare earths may be included in the catalyst. If hydrogen is not added to the feed, Group VIII metals (such as nickel, cobalt, palladium, and platinum) as well as other metals (such as chromium, vanadium, titanium, manganese, and rhenium) may be included in the catalyst. Mixtures of these metals may also be present. Strongly basic metals such as the alkali metals are unsatisfactory as they poison substantially all of the polymerization sites on the molecular sieve. For this reason, the alkali metal content of the molecular sieve is less than 1%, preferably less than 0.1%, and most preferably less than 0.01%. The most preferred substituents for use are zinc and cadmium, of these, zinc is preferred. The amount of zinc or cadmium used is typically from about 0.01 to about 10 wt. %.

The use of zinc or zinc compounds as the substituent on the essentially alumina free materials, gives surprising stability, yields, and activity in the gaseous olefin oligomerization processes described herein.

The polymerization processes of the present invention are surprisingly more efficient with small crystalline particles than with larger crystalline particles. Preferably, the molecular sieve crystals or crystallites are less than about 10 microns, more preferably less than about 1 micron, and most preferably less than about 0.1 micron in the largest dimension. Methods for making molecular sieve crystals in different physical size ranges are known to the art.

The molecular sieves can be composited with inorganic matrix materials, or they can be used with organic binders. It is preferred to use an inorganic matrix, since the molecular sieves, because of their large internal pore volumes, tend to be fragile, and to be subject to physical collapse and attrition during normal loading and unloading of the reaction zones as well as during the oligomerization processes. Where an inorganic matrix is used, it is highly preferred that the matrix be substantially free of hydrocarbon conversion activity.

The reaction zone is typically operated below about 350° C. Above that temperature not only significant cracking and loss of oligomer product take place, but also significant hydrogen transfer reactions causing loss of olefinic oligomers to paraffins and aromatics. Reaction zone temperatures are typically above 50° C. and preferably from 205° C. to 325° C. Hydrocarbon partial pressures for the low pressure oligomerization process range from subatmospheric to about 30 bar and preferably range from atmospheric to about 10 bar. Gas hourly space velocities can range from 10 to 4000 preferably from 20 to about 2000.

The effluent from the oligomerization reaction zone can be recovered and used as gasoline or a number of further processing steps can be performed. All or part of the effluent can be contacted with the molecular sieve catalysts in further reaction zones to further react unreacted alkenes and alkene oligomers with themselves and each other to form still longer chain materials. Of course, the longer the carbon chain, the more susceptible the compound is to being cracked. Therefore, where successive oligomerization zones are used, the conditions in each zone must not be so severe as to crack the oligomers. Preferably, the reaction conditions in each of the succeeding zones are less severe than in the oligomerization zone which immediately precedes it. Operating with oligomerization zones in series with decreasing severity can also make process control of the exothermic oligomerization reactions much easier.

One particularly desirable method of operation is to separate unreacted alkenes present in the effluent from the alkene oligomers present in the effluent and then to recycle the unreacted alkenes back into the feed.

The run life of the catalyst in the oligomerization reaction zone can be greatly and surprisingly increased by periodically stopping the flow of feed into the reaction zone and stripping the catalyst with a stripping gas (such as hydrogen, nitrogen, or water vapor).

FIGURE

The FIGURE shows the $C_5^+$ yields obtained using CZM to oligomerize a propene containing feed. The FIGURE also shows the effectiveness of stripping the catalyst to restore catalytic activity.

EXAMPLE 1 (B3756-26)

A propene feed was contacted with a silicalite containing catalyst (33% silicalite/67% alumina) at 13.8 bar (200 psig) and 371° C. (700° F.). The initial LHSV was 1; at 15 hours the LHSV was raised to 4. The wt % distribution of products was as follows:

| | Hours on Stream | | | |
|---|---|---|---|---|
| | 5 | 15 | 29 | 40 |
| $C_1$ | 0.7 | 0.2 | 0 | 0 |
| $C_2$ | 0.2 | 0.6 | 0.2 | 0.1 |
| $C_3$ | 78.3 | 17.9 | 12.5 | 12.0 |
| $C_4$ | 10.7 | 28.6 | 21.5 | 19.4 |
| $C_5$ | 2.9 | 26.7 | 19.3 | 21.4 |
| $C_6$ | 6.2 | 12.9 | 19.5 | 22.9 |
| $C_7$ | 0.4 | 5.7 | 14.9 | 15.5 |
| $C_8$ | 0 | 3.6 | 10.7 | 7.2 |
| $C_9^+$ | 0 | 0.8 | 0.9 | 0.8 |
| $C_5^+$ | 10.0 | 52.7 | 66.4 | 68.5 |
| $C_5^+/C_3$ Conversion, % | 46 | 64 | 76 | 78 |

A test with the alumina binder alone at LHSV of 4, 371° C. (700° F.), and 13.8 bar (200 psig) gave a maximum $C_5^+$ yield of 3% and a maximum $C_5^+/C_3$ conversion of 4%. A silicalite catalyst which contained over 1% sodium gave results comparable to the alumina binder.

EXAMPLE 2

A propene/propane feed (75/25) was contacted with a silicalite containing catalyst (65% silicalite/35% alumina) at atmospheric pressure 316° C. (600° F.) and LHSV of 2, the product yield was as follows:

| Fraction | wt % |
|---|---|
| $C_1$-$C_2$ | 0.1 |
| $C_3^=$ | 3 |
| $C_3$ | 23 |
| $C_4^=$ | 12 |
| $C_4$ | 2 |
| $C_5$-93° C.(200° F.) | 34 |
| 93° C.-182° C.(360° F.) | 26 |
| $C_5^+$ | 60 |

EXAMPLE 3

A propene/propane feed (75/25) was contacted with a CZM/alumina catalyst (50/50) at atmospheric pressure, LHSV of 2, and 316° C. (600° F.). The $C_5^+$ yield is illustrated in the FIGURE. Periodically the catalyst was removed from contact with the feed and was stripped with a stripping gas to restore oligomerization activity. Stripping gases and temperatures are shown on the FIGURE.

What is claimed is:
1. A process for oligomerizing normally gaseous alkenes, comprising:
    (a) contacting under low pressure oligomerization conditions a feed comprising normally gaseous alkenes with a catalyst comprising an essentially alumina free intermediate pore size silicaceous crystalline molecular sieve having a silica:alumina mole ratio greater than about 200:1, selected from silicalite, CZM, or mixtures thereof; and
    (b) recovering an effluent comprising oligomers of said alkenes.
2. The process of claim 1 in which said oligomerization conditions include a temperature of less than about 325° C.
3. The process of claim 2 wherein said oligomerization conditions include a pressure less than about 30 bar and a temperature above about 50° C.
4. The process of claim 1 wherein said alkenes are propene, 1-butene, 2-butene, 2-methylpropene and mixtures thereof.
5. The process of claim 1, wherein said catalyst further comprises zinc or a compound thereof, cadmium or a compound thereof, or mixtures thereof.
6. The process of claim 1 wherein said molecular sieve has a silica:alumina mole ratio greater than about 500:1.
7. The process of claim 1 wherein said molecular sieve has a silica:alumina mole ratio greater than about 1000:1.
8. The process of claim 1 further comprising the steps of: periodically removing said catalyst from contact with said feed, stripping said catalyst with a stripping gas, and resuming said contacting under oligomerization conditions.
9. The process of claim 1, further comprising the steps of: separating unreacted alkenes present in said effluent from alkene oligomers present in said effluent and recycling said unreacted alkenes into the feed for said contacting step.
10. The process of claim 1, 2, or 3, further comprising the step of: hydrogenating said alkene oligomers.

* * * * *

UNITED STATES PATENT AND TRADEMARK OFFICE
CERTIFICATE OF CORRECTION

PATENT NO. : 4,423,268
DATED : December 27, 1983
INVENTOR(S) : STEPHEN J. MILLER It is certified that error appears in the above-identified patent and that said Letters Patent are hereby corrected as shown below:

Col. 2, line 24, "as effective" should read --an effective--.

Signed and Sealed this

Tenth Day of July 1984

[SEAL]

Attest:

GERALD J. MOSSINGHOFF

Attesting Officer

Commissioner of Patents and Trademarks